United States Patent [19]

Lee et al.

[11] Patent Number: 5,026,653
[45] Date of Patent: * Jun. 25, 1991

[54] SCAVENGER ANTIBODY MIXTURE AND ITS USE FOR IMMUNOMETRIC ASSAY

[75] Inventors: Jin P. Lee, Troy; F. Brad Salcedo, Ann Arbor; Martin F. Robins, Troy, all of Mich.

[73] Assignee: Leeco Diagnostic, Inc., Southfield, Mich.

[*] Notice: The portion of the term of this patent subsequent to Feb. 2, 2005 has been disclaimed.

[21] Appl. No.: 103,067

[22] Filed: Sep. 30, 1987

Related U.S. Application Data

[60] Division of Ser. No. 34,779, Apr. 3, 1987, abandoned, which is a continuation-in-part of Ser. No. 718,921, Apr. 2, 1985, Pat. No. 4,722,889.

[51] Int. Cl.$^5$ .................. G01N 33/543; G01N 33/48; G01N 21/08; G01N 1/48
[52] U.S. Cl. .................. 436/518; 436/524; 436/65; 436/165; 436/807; 436/814; 436/818; 435/7.94; 435/962; 422/58; 422/61
[58] Field of Search .................. 435/7, 810; 436/518, 436/548, 807, 814, 818, 825, 65, 87, 165, 166, 168, 170, 175; 422/58, 61

[56] References Cited

U.S. PATENT DOCUMENTS

| | | | |
|---|---|---|---|
| 4,180,556 | 12/1979 | Kim et al. | 424/1 |
| 4,299,815 | 11/1981 | Hansen et al. | 424/1 |
| 4,514,505 | 4/1985 | Canfield et al. | 436/518 |
| 4,595,661 | 6/1986 | Cragle et al. | 436/534 |
| 4,737,456 | 4/1988 | Weng et al. | 436/518 |
| 4,748,042 | 5/1988 | Linnecke et al. | 422/56 |

*Primary Examiner*—Esther L. Kepplinger
*Assistant Examiner*—Janelle Graeter
*Attorney, Agent, or Firm*—Krass & Young

[57] ABSTRACT

Provided is a test kit for conducting a membrane sandwich immunoassay of a multivalent antigen, optionally including reagents, the test kit includes a hollow container for reception of a fluid specimen, containing in series fluid absorbent body, a fluid pervious layer, and a fluid pervious solid membrane layer on which antibody is immobilized such that fluid added (e.g., labeled antibody and fluid specimen) to the container migrates through the membrane and in the presence of unlabeled scavenger antibody on the reactive surface of the membrane forms a multiple-site immunospecific antibody-antigen-antibody sandwich immobilized and labeled thereon, preferably in the form of a visible positive or negative indicator of the presence and/or amount of the analyte antigen in the specimen sample. The scavenger antibody serves to prevent false positive or other spurious reactions due to antigen analogs, antigen interference substances, or circulating human immnoglobulins.

10 Claims, 6 Drawing Sheets

TYPICAL ANTIBODY ANTIGEN SANDWICH COMPLEX $b_1$ = MONOCLONAL $Ab_1$
$b_2$ = MONOCLONAL $Ab_2$
$b_3$ = MONOCLONAL $Ab_3$
g = ANTIGEN
C = SERUM CIRCULAR ANTIBODY

FALSE POSITIVE, OR ELEVATED WITHOUT SCAVENGER Ab

SCAVENGER ANTIBODY MIXTURE AND ITS USE FOR IMMUNOMETRIC ASSAY

REFERENCE TO RELATED APPLICATION

This application is a division of copending application Ser. No. 034,779, filed Apr. 3, 1987 now abandoned, which is a continuation-in-part of copending application Ser. No. 718,921 now U.S. Pat. No. 4,722,889 filed Apr. 2, 1985.

FIELD OF THE INVENTION

This invention relates to immunoassay methods for detecting and/or determining the concentration of antigenic substances in fluids such as serum or urine and to assay kit apparatus for use therein. In another aspect, it relates to immunometric assay techniques.

In yet another aspect, it relates to the following novel ideas:

(1) The use of a specifically designed reaction container for conducting sandwich immunoassays.

(2) The use of a solid reaction surface (plastic bead, test tube, plastic membrane, and the like) containing or supporting multiple monoclonal antibodies or a mixture of polyclonal antibody and monoclonal antibody.

(3) The formulation of antibody-enzyme conjugate to contain a compatible substrate enhancer.

(4) The use of a visualization indicator means whereby in membrane sandwich immunoassays a visual plus sign or endpoint is observed in positive samples and a minus sign is seen in negative samples.

(5) The use of scavenger antibodies to remove any possible cross reactivity and reduce possible prozone reactions.

(6) The use of a specific volume and concentration of substrate to accomplish a simultaneous color development and removal (wash) of unattached reactants.

BACKGROUND OF THE INVENTION

Immunometric assays (also called "sandwich assays") using specific antibodies for the determination of the presence and/or concentration of antigenic substances in fluids are well known.

In such an assay, the amount of labeled antibody associated with a complex is directly proportional to the amount of antigenic substance in the fluid sample, illustrated as follows:

(solid support)-$Ab_1$ + Ag + $Ab_2$-Tracer $\longrightarrow$
1st Antibody    endogenous    2nd antibody
                antigen solid-$Ab_1$—Ag—$Ab_2$-Tracer
Bound complexes This assay which is a "two site" or "sandwich" assay because two non-interfering epitopic sites of the antigen are bound, is described by Wide, "Radioimmunoassay Methods", edited by Kirkham and Hunter, E. & S. Livingston, Edinburgh, 1970, pp. 199–206. Such immunometric assays have been found to be effective for the detection of polyvalent antigen or antibody, i.e., an antigenic substance that is able to complex with two or more antibodies at the same time.

In an attempt to alleviate problems present in the prior art, a method is described by David et al., in U.S. Pat. No. 4,376,110, wherein the polyclonal antibody used in an immunometric assay is replaced by at least one and usually two different monoclonal antibodies, each specific for a single, unique epitope or antigenic site. According to the conventional method, the epitope-specificity of the monoclonal antibody to be coated to the solid support should be different from the monoclonal antibody used for the labeled antibody. The two monoclonal antibodies should bind the antigenic substance at sites remote from each other so that the binding of one antibody will not interfere with the binding of the other.

Many problems have been encountered by reasearchers using the above technique when monoclonal antibodies produced by one or two cell lines are used in the two site sandwich immunometric assay. The assay has suffered from several problems:

1. Lack of low end sensitivity.

At the end of the standard range, the assays may not detect very low levels of analyte. This is particularly true for hepatitis B surface ($HB_s$) antigen and glycopituitary hormones such as human chorionic gonadotropin (hCG), thyroid stimulating hormone (TSH), luteinizing hormone (LH), and follicle stimulating hormone (FSH). This shortcoming leads, for example, to inability to detect a recent hepatitis infection, or to inability to distinguish normal thyroid function from hyperthyroid function, or conceivably may result in a failure to detect a dangerous ectopic pregnancy.

2. Lack of Accuracy.

Interference occurs in TSH assays run on pregnant patient serum. The structure of one of the subunits of hCG is very similar to a TSH subunit. If present in the serum, the hCG will bind to the monoclonal antibody on the solid carrier and prevent the binding of TSH, which is normally found in very low levels. The labeled monoclonal antibody in solution will not bind to the hCG to complete the "sandwich," so the result is negative, regardless of the actual TSH value.

In an hCG assay, only the intact hCG beta molecule will be recognized by both the solid carrier monoclonal antibody and the labeled monoclonal to complete the "sandwich". However, beta subunits may be found in the serum in cases of hydatidiform mole, choriocarcinoma and any other malignant melanoma and will not be detected by this assay.

3. Hook effect (or prozone phenomenon).

It is well-known that concentration of hCG in pregnancy often exceed 100,000 mIU/ml. Therefore, an assay must give reliable results at high concentrations of hCG. However, a sandwich assay using one monoclonal antibody that is labeled and one on the solid carrier may suffer from a hook effect. The hook effect occurs when high levels of hCG saturate the monoclonal antibody binding sites, disallowing the completion of the sandwich, and "hooking" the results down to a lower level. A very high hCG sample may actually test as negative.

4. Interference.

The presence of non-analyte antibody-binding substances in patient serum has been found by many laboratories to cause a false increase in analyte concentrations when sandwich assays are used. These binding substances may be antibodies which mimic the analyte by binding both the antibody on the solid carrier and the soluble labeled antibody.

This cross-reaction may occur with monoclonal antibodies or with other antisera when antibodies from the same species are used for both the solid phase and the soluble labled phase. The occurence of antibody directed cross-reactivity against monoclonal antibody sandwich assays has been reported for TSH, hCG, carcinoembryonic antigen (CEA), hepatitis A and hepatitis B, prolactin, LH and FSH.

5. Complicated reaction devices

The prior art has required trained technical personnel with specialized laboratory equipment to perform immunoassays. Small and accurately dispensed amounts of reactants had to be reproduceably aliquoted and quantitation required sophisticated spectrophotometric detection instrumentation.

6. Instability of reagents

Refrigerated storage of components was necessary to extend the shelf life of reagents beyond a few weeks. For example, in case of the enzyme substrate 5'-bromo-4-chloro-3-indoxylphosphate (BCIP), the substrate requires a color enhancer such as Nitro-Blue tetrazolium chloride (NBT) for optimum color development. The chemical combination of these two ingredients results in a thermally labile mixture.

7. Extra steps

Previous applications required an additional wash step prior to the addition of the substrate to remove the excess antibody-enzyme conjugate before reaction with the enzyme substrate.

Examples of conventional "sandwich" immunoassays for various antigens such as alpha fetoprotein (AFP), hCG, TSH, LH, FSH, IgE, and hepatitis B-surface antigen are of the following types:

1. Two site immunoassay based on two polyclonal antibodies, one of these antibodies being immobilized on a solid phase and the other being in soluble labeled form.

2. Two site immunoassay based on two monoclonal antibodies directed against two separate and distinct epitopes of the antigen, one of these antibodies being bound on a solid phase and the other being of soluble labeled form (David et al., supra).

3. Two site immunoassay based on one monoclonal antibody and one polyclonal antibody, the monoclonal antibody being bound on a solid phase and the polyclonal antibody being in soluble labeled form.

In view of the mentioned shortcomings, only trained personnel in well equipped clinical laboratories can perform traditional sandwich enzyme immunoassays. Even qualitative assays can result in equivocal answers because of potential misinterpretation of the gradient of color reactions near the cutoff concentration. Thermal instability of commonly employed reagent combinations require refrigerated storage, and incomplete "washing" can yield high background and spurious results.

The conventional forward or reverse assay using the monoclonal-monoclonal antibody sandwich assay system (David et al., supra) is time consuming, and is not well suited to determination of small concentrations of antigen since formation of a sandwich of the antigen involves only two matching epitopes of the monoclonal antibody. The occurrence of false positive (false elevated) or false negative (false lower) values can be due to the nature of the monoclonal-monoclonal paired antibodies and to the cross reactivity of non-related antigen or antigen similar substances.

The conventional monoclonal-monoclonal antibody sandwich simultaneous assay (as opposed to the forward or reverse assay) also has the potential for a hook effect since the number of soluble labeled antibody molecules is limited.

Accordingly, one object of the present invention is to provide an improved process for the sandwich or two-site immunometric assay for antigenic substances.

An object of the present invention is to provide more rapid, more specific and more accurate immunometric assay techniques.

Another object of the present invention is to provide more sensitive immunometric assay techniques.

Another object of the present invention is to provide improved "simultaneous" immunometric assays.

Another object of the invention is to create a simple reaction device for immunometric assays which can be utilized without special equipment or training.

Another object of the invention is to create an enhanced color reaction in a thermally stable reagent configuration.

Another object of the invention is to present the end point of the reaction in an easily interpreted manner with virtually no potential for equivocal results.

Another object of the invention is to eliminate the washing step for membrane based immunoassay procedures.

The manner in which these and other objects are realized by the present invention will be apparent from the summary and detailed description set forth below.

SUMMARY OF THE INVENTION

This invention uses a novel concept of combining monoclonal antibody and polyclonal antibody in an immunometric assay. In one embodiment, unlabeled antibody is bound to a solid support, monoclonal antibody (one or more than one) is used as the soluble labeled antibody, and unlabeled multiple monoclonal antibody or polyclonal antibody as scavenger antibody. In another embodiment, multiple epitope specific monoclonal antibodies are used in an immunometric assay as the unlabeled antibody bound to a solid support. Polyclonal antibody is used as the soluble labeled antibody, and unlabeled multiple monoclonal antibody is used as scavenger antibody. Each antibody is specific to a single distinct antigenic site produced by clones derived from a unique hybridoma cell line. In a preferred embodiment of the invention, the multiple monoclonal antibody used as the antibody bound to the solid support is the product of several hybridoma cell lines with different epitope specificities which are distinct both from the monoclonal antibody used for the labeled antibody and from the specific monoclonal antibody used as scavenger antibody.

The Scavenger Antibody

The literature to our knowledge has not reported a multiple-site immunoassay based on multiples of different monoclonal antibodies directed against multiple distinct and separate epitopes on said antigen, two of these antibodies being on a solid phase, another one or more in soluble labeled form, and still another antibody (which is extraneous to the primary antibodies binding the antigen) here termed a "scavenger antibody" which comprises one or more substances selected from antigen analogs, antigen interference substances, and circulating immunoglobulins of human origin. This antibody is in unlabeled form for binding against cross-reacting antigen or unrelated antigen, or human IgG, IgM, and IgE, and is in soluble form. The scavenger antibody has at least three variations, for example:

1. Three-site or more than three-site (multiple-site) immunoassay based on antigens having three or multiple separate and distinct epitope binding sites for antibodies, two of these antibodies being antigen-specific bound on a solid phase and one or more in soluble labeled form, and a scavenger antibody comprising one or more than one monoclonal antibody (e.g., mouse IgG, or IgM or IgE) in soluble unlabeled form as scavenger antibodies which are immunospecific to anti-mouse human antibodies, sometimes referred to herein as serum circulating antibodies.

2. A three-site or more than three-site immunoassay based on three monoclonal antibodies directed against three or more than three separate and distinct epitopes, and a polyclonal antibody mixture. One of the monoclonal antibodies and the polyclonal antibody mixture is bound on a solid phase, and the other two monoclonal antibodies are in soluble labeled form. One monoclonal antibody or more than one monoclonal antibody (or mouse IgG or IgM) is in soluble unlabeled form as a scavenger antibody which is immuno specific for binding sites on antigen analogs, cross-reactants and/or anti-mouse human antibodies.

3. A three site or multiple site immunoassay based on: three or multiple monoclonal antibodies directed against three or multiple separate and distinct epitopes, and a polyclonal antibody from different species of animals. Two of the monoclonal antibodies are bound on a solid phase. The other monoclonal antibody or antibodies and the polyclonal antibody are in soluble labeled form. One or more than one monoclonal antibody (e.g., mouse IgG or IgM) is in soluble unlabeled form as a scavenger antibody which is immunospecific for binding sites on antigen analogs, cross-reactants and/or anti-human antibodies.

Further concerning the literature, no references have been found which describe the separation of an enzyme enhancer such as Nitro-Blue tetrazolium (NBT) from the substrate component and its lyophilization in combination with an alkaline phosphatase-monoclonal antibody conjugate to create a stable set of reaction components. Also, no plus-or-minus visualization method has been described which includes immobilization of the anti-analyte monoclonal antibodies onto a solid nylon membrane surface in the form of a vertical line and the immobilization of an antibody directed against the IgG fraction from the host species utilized in the enzyme conjugate in the form of a horizontal line thus creating either a visible plus or minus following addition of substrate. Also, no literature has described the exact titering of the substrate solution in a proportion to the other reactants so that it contemporaneously accomplishes a removal of excess conjugate from bound surfaces and achieves the necessary chromogen reaction with bound enzyme.

By way of further summary and in another preferred aspect, a membrane apparatus is provided optionally in a test kit with reagent formulated so that an enzymeimmunometric reaction on the membrane surface creates a visually distinct positive or negative sign. The reagent is packaged in premeasured aliquots, and the membrane apparatus according to the invention is in a unique user friendly configuration. The apparatus includes a membrane having reactive surfaces for reception of a fluid sample, a filter screen, an absorbent body to receive the fluid sample and test reagents, and a housing container to support the reactive surfaces and contain the fluids.

DETAILED DESCRIPTION OF THE INVENTION

In accordance with the present invention there are provided improved sandwich immunoassay methodologies and kits for use wherein all the advantages possessed by the prior immunoassays are maintained with low end sensitivity and increase in specificity, but with concurrent avoidance of the hook effect.

In general, the present invention encompasses an improved sandwich immunoassay for an antigenic substance (Ag) in a fluid. As used herein, the term antigen or antigenic substance refers broadly to substances to which antibodies can be produced. Among such substances may be mentioned haptens, hormones such as human thyroid stimulating hormone (HTSH), human luteinizing hormone (HLH), and human follicle stimulating hormone (HFSH), human prolactin, insulin, gamma globulins, allergens, viruses and virus-subunits, bacteria, toxins such as those associated with animal venoms, and the like. Among the specific antigens which may be assayed by the process of the present invention may be mentioned human chorionic gonadotropin (hCG), human thyroid stimulating hormone (HTSH), carcinoembryonic antigen (CEA), hepatitis B surface antigen and IgE.

The monoclonal antibodies useful in the present invention may be obtained by the process discussed by Milstein and Kohler and published in Nature 256, 495-497, 1975. The details of this process are well known and will not be repeated here. However, basically the process involves injecting a mouse with an immunogen. The mouse is subsequently sacrificed and the spleen removed and teased apart, and the resultant cells are combined with myeloma cells in a specific ratio. The combined cells are induced to fuse by adding polyethylene glycol. The result is a hybrid cell referred to as a "hybridoma" that reproduces in vitro. After screening, the hybrid cells of interest are further screened to isolate individual clones each of which secrets a single antibody species specific for the antigen. Accordingly, after the different hybridoma cell lines are screened to identify those that produce antibody to the desired antigen, the antibodies produced by the individual hybridoma lines are identified by their affinity to the immunogenic substance. Selection is based on the following criteria:

(a) monoclonal antibody selected for the solid phase has an affinity of $10^8$ to $10^{12}$ liters/mole.

(b) monoclonal antibody selected for the soluble labeled form has an affinity of $10^6$ to $10^{12}$ liters/mole.

(c) monoclonal antibody selected for the scavenger antibody has an affinity of $10^2$ to $10^{12}$ liter/mole. The invention is based on the discovery that mixing scavenger antibodies with multiple monoclonal antibodies directed against various epitopes of antigen or with monoclonal antibodies paired with polyclonal antibodies in a two site sandwich immunoassay can:

1. increase the sensitivity of antigen binding assays
2. eliminate the cross reactivity of antigen analogs
3. eliminate the interference of circulating antibodies in human serum sample, and
4. eliminate interference from analogs of the antigen.

The Simultaneous Assay

Because the two site immunometric assay relies upon formation of an antibody-antigen-antibody sandwich, usually at least two different pairs of monoclonal antibodies, or one monoclonal antibody paired with polyclonal antibodies are used. Each pair is selected so that the antibodies of the pair do not interfere with the binding of each other to the antigen. The selection is made as to both the bound antibody pair and the soluble labeled antibody pair. In a simultaneous sandwich assay, in which the immunoabsorbent utilizes multiple immobilized antibodies, the sample labeled soluble antibody or antibodies and scavenger antibody or antibodies are incubated simultaneously in one incubation step.

The use of a simultaneous assay is by far the preferred one. This type of assay brings about ease of handling, homogeneity, reproducibility, linearity of the assays and high precision. The sample containing antigen, solid phase immunoabsorbent (with immobilized antibodies) and labeled soluble antibody or antibodies, and the unlabeled soluble scavenger antibody or antibodies, are incubated under conditions and for a period of time sufficient to allow antigen to bind to the immobilized antibodies and to the soluble antibody or antibodies. In general, it is desirable to provide incubation conditions sufficient to bind as much antigen as possible. Since this maximizes the binding of labeled antibody to the solid phase, it therefore increases the signal. However, it is also desirable to provide an optimal incubation condition sufficient to make the scavenger monoclonal antibody or antibodies bind as much of the antigen analog or interfering substance as possible to avoid their binding to the reagent antibody or antibodies.

The Sequential Assay

Another preferred embodiment includes an immunometric assay for the determination of the presence of an antigenic substance in a body fluid comprising sequential assay steps. These include sequentially contacting a sample of the fluid with immobilized antibodies, scavenger antibodies, and labeled antibodies (as described), incubating, separating the solid phase, and determining or measuring the analyte. Each antibody has an affinity for the antigenic substance or interference substance in a range from $10^2$ liters/mole to $10^{12}$ liters/mole. The immobilized antibodies are bound to a solid carrier insoluble in the body fluid, and the labeled antibodies and scavenger antibodies are soluble in the fluid.

The assay of the invention preferably should use more than one monoclonal antibody as scavenger antibody. Mixtures containing two, three, four or more scavenger antibodies each of which binds to separate and different antigenic sites on the antigen analog, or other interfering substance, thus are employed.

The process is preferred for analytes such as IgE, hepatitis A, hepatitis B, hepatitis non A/non B, abuse drug, alphafetoprotein, carcinoembryonic antigen, rubella antibody and rheumatoid autoimmunoglobulin.

The term "abuse drug" is defined as including one or more of the following: amphetamines, barbiturates, methadones, opiates, cocaine and its metabolites, cannabinoids, benzodiazepine compounds, PCP (phencyclidine), propoxyphene, and alcohol.

Various types of interfering substances can be eliminated in assays employing mixtures of suitable monoclonal antibodies. The invention is particularly suited for detection of polypeptide antigens where the antigenic sites are different and have distinct amino acid sequences contained within the polypeptide. However, the amount and type of scavenger monoclonal antibody required for complete elimination of interference is expected to depend on the titer and specificity of the binding substances. Examples of polypeptide antigens of this type are (a) the sequence related hormones including human chorionic gonadotropin (hCG), follicle stimulating hormone (FSH), thyroid stimulating hormone (TSH) and luteinizing hormone (LH), (b) hepatitis B surface antigen adw/ayw, (c) CEA (Carcino Embryonic Antigen). NCA (nonspecific cross-reacting antigen), and the like. Preferred polypeptides analytes are LH, FSH, TSH, IgE, IgG, hepatitis A, hepatitis B, hepatitis non A/non B, alphafetoprotein, carcinoembryonic antigen, insulin, ferritin, glycohemoglobin Al$^C$, prolactin, thymosin peptide, and HTLV-Type III antibody or antigen.

In order to obtain maximum amounts of scavenger antibody bound antigen, the amount of each antibody can be determined by routine experimentation. The precise amount may vary widely depending upon its affinity for the interference antigen. The amount of each scavenger antibody also may vary widely depending upon the antibody used for the solid support and the labeled antibody.

In the preferred mode for performing the assays, certain scavenger antibodies are provided in the incubation medium (usually added with the labeled soluble antibody). The scavenger antibodies are added to assure that nonspecific interfering substances (which are present in the sample and apt to yield false positive or false negative results) can be completely eliminated. The selection of the scavenger antibodies therefore adds substantially to the specificity of the assays described in the present invention.

It has been found that a number of specific monoclonal antibodies (against human IgG, IgM, IgE) can be used as scavenger antibodies for the two-site double sandwich immonoassays. The concentration of the scavenger antibody (normally 1-200 micrograms/microliter) is important in order to maintain the proper sensitivity and inhibit any unwanted interference by mutually occurring cross-reactive proteins in human serum.

The multiple monoclonal antibody or polyclonal antibodies used in the present invention to extract the antigenic substance from the sample being tested can be bound to a water-insoluble carrier. Among these may be mentioned plastic beads, filter paper, porous membranes made from suitable material such as polyvinylidine difluoride or nylon, or test tubes made from polyethylene, polystyrene, polypropylene, or other suitable material. The immobilized antibodies can be either covalently bound or physically bound to the solid phase immunoabsorbent. The techniques for such bonding are well-known to those skilled in the art. In the case of polyclonal antibodies, the covalent binding of the antibodies to the solid phase is preferred.

The labeled monoclonal antibody or polyclonal antibody used in the present invention may be provided with the same labels used in art-recognized immunometric assays. Among these may be mentioned fluorogenic labels for detection by fluorimetry. Suitable fluorescent materials are, for example, fluorescein isothiocyanate and rhodamine isothiocyanate. Among the enzyme labels are horseradish peroxidase, alkaline phosphatase, beta-D-galactosidase, glucose oxidase and urease. Common radiolabels are $I^{125}$, $I^{131}$, $H^3$ and $C^{14}$.

In one preferred adaptation of the enzymeimmunoassay employing an enzyme-antibody conjugate where the enzyme is alkaline phosphatase, the alkaline phosphatase is developed with an enzyme substrate such as BCIP (5'-Bromo-4-chloro-3-indoxylphosphate). The reaction is aided by a substrate enhancer such as NBT (Nitro-Blue tetrazolium chloride). The latter component is presented by means of its inclusion in the enzyme conjugate constituent. Approximately 0.3% of Nitro-Blue tetrazolium chloride is premixed with the appropriate concentration of enzyme-conjugate, and the combination is prealiquoted and lyophilized. When used in an assay, the dried mixture is reconstituted with fluid. The antigen aliquot is introduced into the reaction immediately following its reconstitution and, in this manner, the deleterious effects of combining NBT with BCIP are avoided.

In a typical assay, the amount of labeled antibody associated with the insoluble sandwich complex is determined by examination of the insoluble carrier material by enzymatic, radiolabeled or fluorogenic labeled assay.

The antigens capable of determination using the process of the present invention are "multivalent antigens." The term "multivalent antigen" is meant to include an antigen having at least two different epitopes capable of specific interaction with antibody binding sites. Normally, it is necessary that at least two different epitopes be sufficiently separated from one another so as to allow simultaneous binding of a different immobilized antibody to each of said epitopes. In order for the scavenger antibodies to effectively eliminate the interference antigen or cross reactant, (a) the scavenger antibodies must have a high affinity constant and competitively inhibit the cross-reactant which is turn must have a multiplicity of epitopes accessible to the scavenger antibodies (b) the non-specific epitopes of the immobilized antibody (solid phase) and labeled antibody must be completely inhibited by the scavenger antibodies, and (c) the steric interference substance or cross reactant to the primary antibody (or antibodies) must be eliminated by the binding of the scavenger antibodies.

Any multivalent antigen can be detected by the method of the present invention. This includes viral antigens such as hepatitis surface antigen (HBsAg), Herpes Simplex viruses, measles virus, HTLV Type I, HTLV Type III, and rubella, and other entities such as HCG, TSH, LH, FSH, AFP, CEA, IgE, IgG, prolactin and bacterial entities.

Each antibody in the immobilized combination should have a high affinity for the multivalent antigen (e.g. ranging from $10^7$ to $10^{13}$ liters/mole). Also each antibody should exhibit as high a specificity for the antigen as possible. Scavenger antibodies should be highly selective towards the antigen analog, interference substance, or structurally similar antigen. The specificity and affinity can be optimized in art-recognized ways by routinely carrying out binding experiments of soluble antibody supernatant with labeled antibody and known multivalent antigen.

The sandwich assays of the invention using the combination of antibodies described, can be varied widely in art-recognized ways. Thus, the invention contemplates use of automated or visual techniques known to those skilled in the art of sandwich immunoassay.

In a preferred visual technique, the primary antianalyte combination is covalently bonded to a nylon membrane surface in the form of a vertical line. An antibody mixture raised against the IgG fraction of the monoclonal antibody employed in the enzyme conjugate is also bonded to the nylon membrane in the shape of a horizontal line intersecting the vertical line in the middle. Thereby, the addition of an analyte-free solution followed by enzyme conjugate and substrate will result in a visual minus while the presence of analyte will cause a resultant plus sign.

In a further preferred adaptation of this concept, the enzyme substrate solution is titered to a specific concentration which causes unbound enzyme conjugate to be washed through the membrane and absorbed by the filter material below, while at the same time activating the color reaction necessary for visualization of the bound reactants.

Monoclonal antibody to antigen is obtained using the method of Milstein and Kohler discussed above. The recommended procedure for the production of polyclonal antibodies, is a routine or standard, one employed by most laboratories, the specifics of which can be found in the Handbook of Experimental Immunology edited by D. M. Weir.

DETAILED DESCRIPTION OF THE PREFERRED EMBODIMENTS

Figure 1:
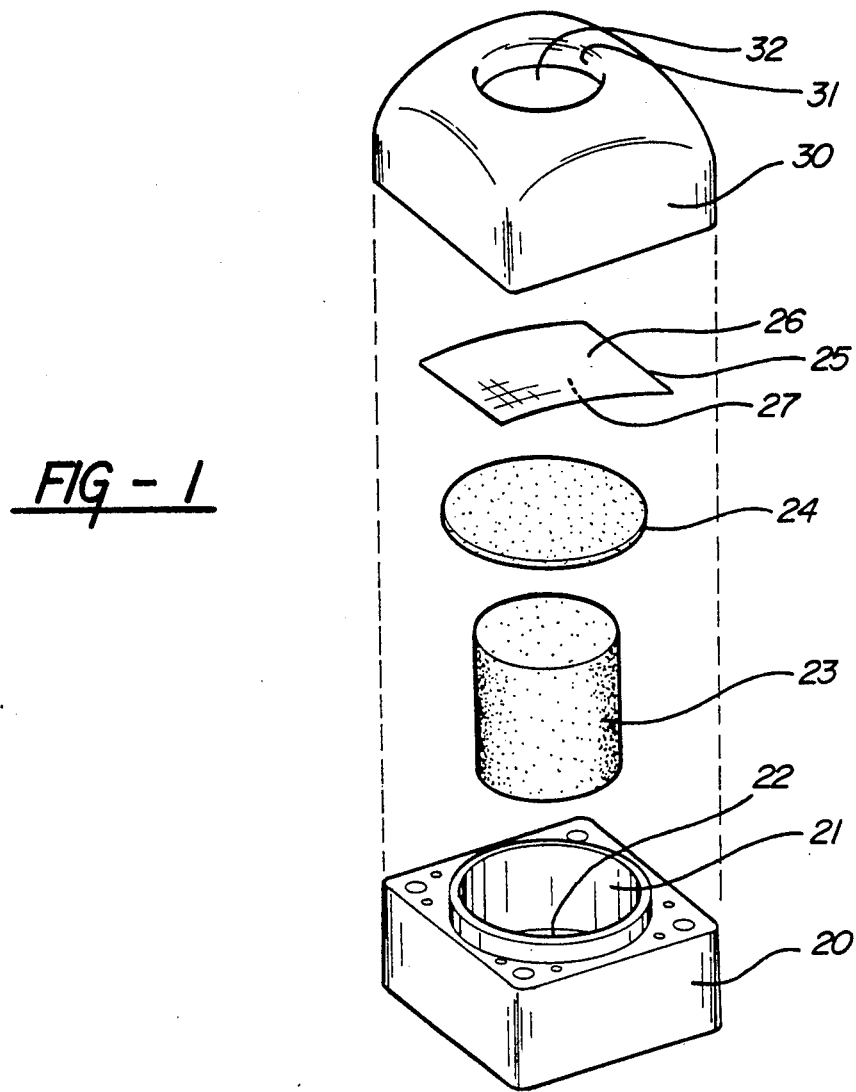
FIGS. 1 and 10 are views of different preferred embodiments of an immunoassay container device according to the invention.

In an apparatus or device aspect according to a preferred embodiment, the invention relates to a test kit for conducting a membrane sandwich immunoassay of an antigen. The test kit comprises a hollow assay container having a top, a bottom, and margins defining a fluid inlet opening at the top adapted to receive and allow entry of a fluid sample into the container for confining the same therein. Within the hollow of the chamber, elements in series are located, held together preferably under compression, in contiguous layered relation. The elements include a fluid absorbent body covered by a fluid pervious layer which in turn is covered by a coextensive fluid porous solid membrane layer having upper and lower surfaces. A portion of the upper surface is coated with bound, unlabeled antibody, the membrane layer being disposed sealingly with said margins such that all fluid sample received at the opening is caused to contact and pass in turn through both the membrane layer and the fluid pervious layer into the fluid absorbent body.

Preferably, the assay container has separate cap and body parts that are adapted to be assembled together to form a single fluid confining container.

The assay container in a preferred embodiment is in combination with a pre-filter closure configured in a funnel-shape having a fluid inlet opening fitted with a filter adapted to screen out solid particulates contained in fluid dispensed into the inlet opening, the closure being dimensioned to close the inlet opening of the assay container and adapted to be inserted into and removed from said container opening.

The closure preferably is a composite of mateable male and female parts having therebetween in mated assembly a solid fluid porous sheet or membrane of filter material.

In a preferred embodiment, the test kit includes an enzyme reagent container separate from the assay container containing enzyme labeled antibody conjugate that is immunospecific and in quantity sufficient to react with the antigen in admixture with scavenger antibody and preferably with an enzyme substrate enhancer.

Preferably the test kit includes a substrate reagent container separate from the enzyme reagent container, containing a substrate (e.g., an aqueous solution of an indoxyl phosphate compound) for the enzyme-antibody conjugate in a quantity sufficient to enable the detection of a positive reaction for the presence of said antigen.

Preferably, the enzyme is alkaline phosphatase and the enhancer comprises an alkaline phosphatase enhancer.

Preferably, the membrane bound substance is an antibody or it may be an antigen or a nucleic acid oligomer.

Referring to the drawings, in a preferred embodiment the assay container 10 (FIG. 3) has a top or cap part 11 and bottom or body part 12. An opening at the top is sealed by a closure 40 also having an opening 43. The closure is provided with a finger tab 45 for grasping and removing the closure from the container to expose the open surface of a reaction membrane 25 (FIG. 4c).

As seen in FIG. 1, the body part has an open cup shaped chamber 21 closed at the bottom surface 22 for containing liquid (i.e., fluid) sample. The cap part 30 has a circumferential margin 31 at the top defining an opening 32 through which fluid sample or reagent is received.

In the body chamber 21, fluid pervious elements are assembled in stacked, contiguous relation, preferably under slight compression (with the cap and body parts assembled as in FIG. 3) so that the upper surface 26 of the uppermost element which is the membrane 25 is touching the underside of the cap margin 31. The elements are a fluid absorption body 23 which may be unitary or a composite or in layers, a fluid pervious layer 24, and a reaction membrane 25 as mentioned above. The membrane has an upper surface 26 and a lower surface 27. A portion of the upper surface has a coating of antibody or is treated with antibody which in preferred embodiment is a horizontal bar line 28 or vertical bar line 29 (FIGS. 4a and 4b).

The closure 40 has a top part 41 and a bottom part 42 with integral funnel-shaped flanges (44,54) and hollow barrel parts (46,56) which telescope together in an interference fit or press fit. Between the top and bottom closure parts (41,42) first and second fluid pervious filter disks (48,49) are located, these preferably being made of fiber glass filter material and microporous filter paper, respectively. In a preferred embodiment, the first filter has porosity such that it screens out solid particles in the sample from entering the container. The second filter has microporosity such that the linear flow rate is controlled so that it is in phase with the intended immunometric reaction times. When assembled, the disks are held together against dislodgement or leakage at the edges by friction fit of the disks between the telescoped closure barrel parts (46,56). When the closure is inserted into the assay container inlet opening, the extent of its insertion is advantageously such that the filter layer 49 either touches or is closely adjacent to the container membrane 25. The lower barrel 56 is provided with circumferentially spaced fins 58 which in closure relation with the assembled cap 30 and body 20 have a friction fit against the margin 31 of the cap opening. Fluid introduced to the fluid inlet 43 is funneled down through the filter disks (48,49), is passed out through the fluid outlet 55 onto and through the membrane 25 and the pervious layer 24 into the fluid absorption body 23.

In another preferred embodiment (FIG. 10), the assay container has a top or cap part 30a and bottom or body part 20a. An opening 32a at the top is sealed by a closure 40 (see FIG. 3) also having an opening 43. The closure is provided with a finger tab 45 for grasping and removing the closure from the container to expose the open surface 26a of a reaction membrane 25a.

Figure 10:
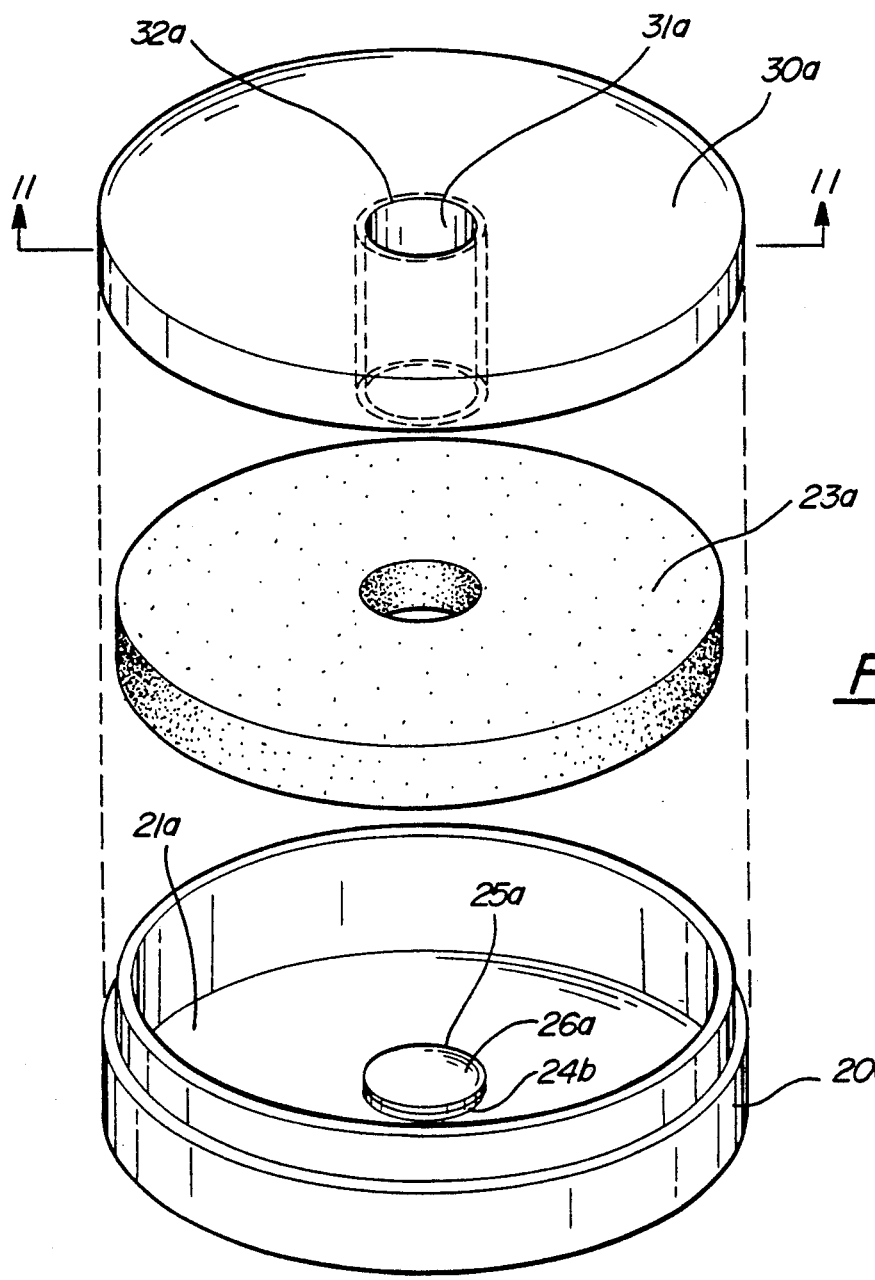

As seen in FIG. 10, the body part has an open cup shaped chamber 21a closed at the bottom surface 22a for containing liquid (i.e., fluid) sample. The cap part 30a has a circumferential margin 31a at the top defining the opening 32a through which fluid sample or reagent is received.

Figure 2:
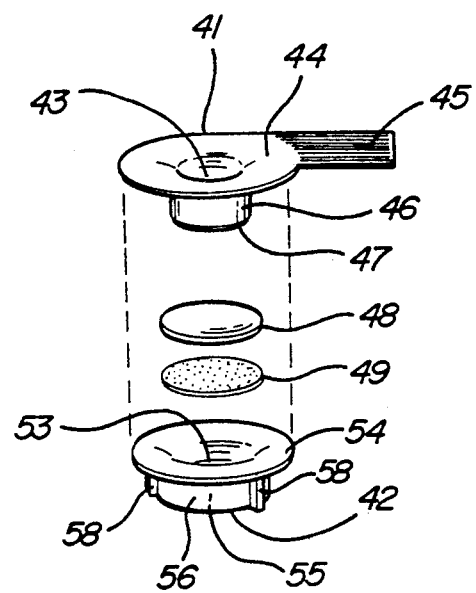
FIG. 2 is a view of a preferred closure for the container devices of FIGS. 1 and 10.
Figure 11:
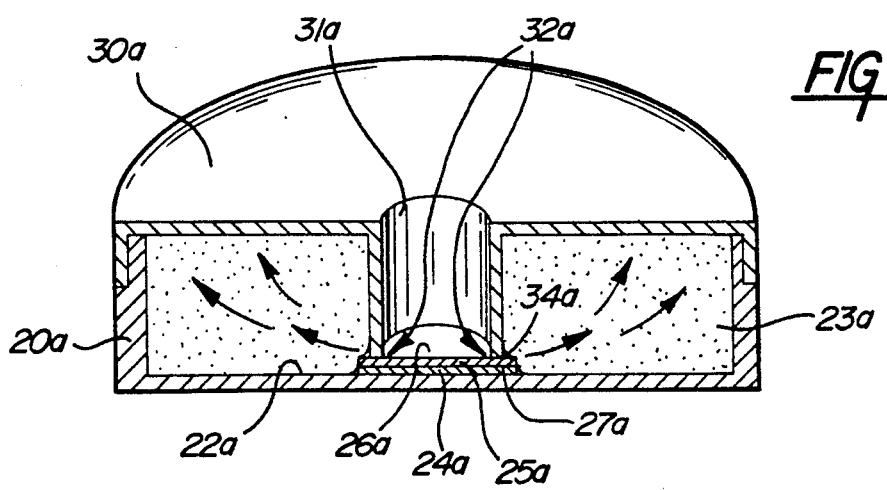
FIG. 11 is a view in cross section of the device of FIG. 10 taken on line 11—11.

In the body chamber 21a, a fluid pervious planar absorption body and a membrane (23a, 25a) are assembled in coaxial, contiguous relation, with the cap and body parts assembled as in FIG. 11 so that the upper surface 26a of the membrane 25a is close to or touching the rim 34a of the cap margin 31a. The elements receiving assay fluid through the opening 32a (with the direction of radially outward and upward fluid flow shown by the arrows in FIG. 11) are the fluid absorption body 23a which may be unitary or a composite or in layers, and the reaction membrane 25a as mentioned above. The membrane has an upper surface 26a and a lower surface 27a optionally in contact with the bottom surface 22a or in a preferred embodiment, the lower surface 27a is in co-extensive contact with a fluid pervious disc or layer 24a the undersurface of which in turn is in contact with the container bottom surface 22a. A portion of the upper surface has a coating of antibody or is treated with antibody which in preferred embodiment is a horizontal bar line 28 or vertical bar line 29 (FIGS. 4a and 4b). The closure 40 (FIGS. 2 and 3) can be used to close the container opening 32a. When the closure is inserted into the opening, the extent of its insertion is advantageously such that the filter layer 49 either touches or is closely adjacent to the upper surface 26a of the container membrane.

The structural parts of the devices of the invention can be made of any suitable materials such as glass, rigid or flexible polymeric plastic materials, cellulosic material, and the like. The pervious filters preferably are made of polyester, fiberglass, microporous cellulose filter paper, microporous non-activated nylon membrane, and the like. The active membrane preferably is made of nylon, nitrocellulose, latex particles, cellulose acetate, polyester and nylon polyester and cellulose nitrate, polysulfone, and the like. The fluid absorbent body preferably is cellulose paper, cotton filtron or other suitable absorbent material.

In a preferred embodiment, the absorbent body material is desiccated, preferably by vacuum drying, and the assay device containing the dried absorbent body is packaged optionally with a drying agent such as silica gel in a water-impervious envelope prior to use so that the packaged device remains dry and thus has a long shelf life prior to use thereof.

The disk or separating member (24, 24a) of porous polyethylene, fiberglass or other material, preferably material which is antibody-inert, i.e., does not bind antibody, in a preferred embodiment is made to contain any enzyme inhibitor such as a chelating agent, e.g. EDTA, in an amount sufficient to react with enzyme in the absorbent body (23, 23a) and to thereby inhibit or prevent the back-flow or reverse diffusion of unbound or soluble enzyme-labeled material into the membrane (25, 25a) where during the read-out in the presence of enzyme substance and chromophore, the enzyme migration could falsely develop unwanted color change on the membrane upper surface (26, 26a) even a modest color change which is uniform over the entire visible surface. In other words, the advantage gained is significant because in the read-out phase, it maximizes the sharpness of the visual signal, especially as to the contrast between the antibody coated or color portion and the uncoated or colorless portion of the membrane surface.

Having now generally described this invention, the same will be better understood by referring to the following examples. The examples are for purposes of illustration only and are not intended to limit the invention.

EXAMPLE 1

(A) hGC (Simultaneous Assay)

Figure 5:
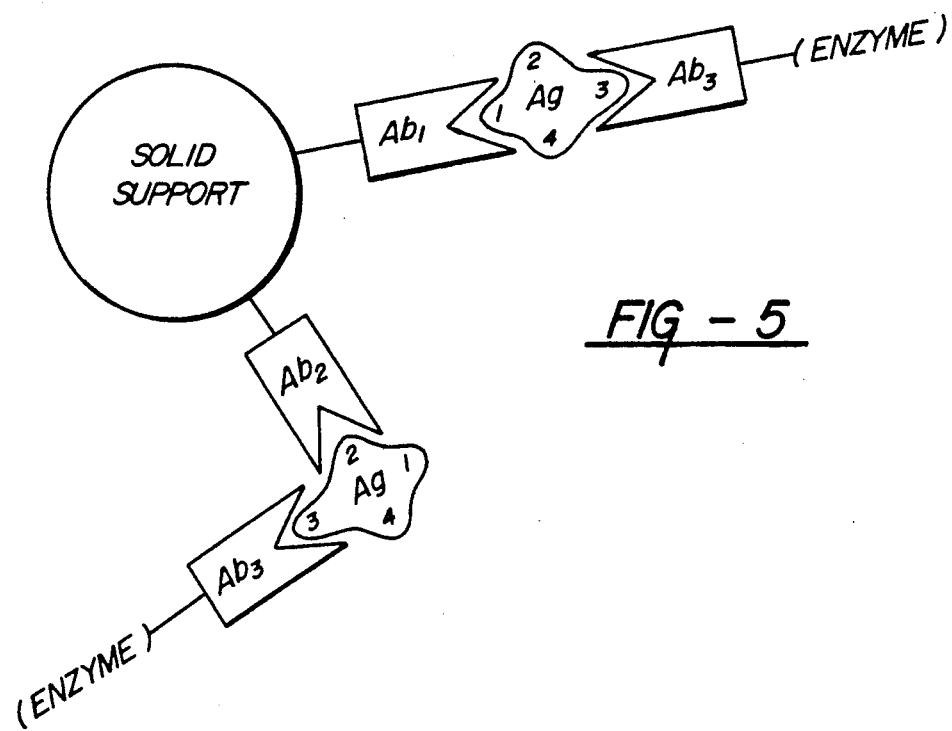
FIGS. 5, 6 and 7 are diagrammatic representations respectively of a conventional enzyme-antibody antigen sandwich complex; a false positive or elevated complex (without scavenger antibody); and an enzyme-antibody antigen sandwich complex in the presence of scavenger antibody according to the invention, such that serum circular antibody, antigen analogs and cross-reactant substances are eliminated from the complex.
Figure 6:
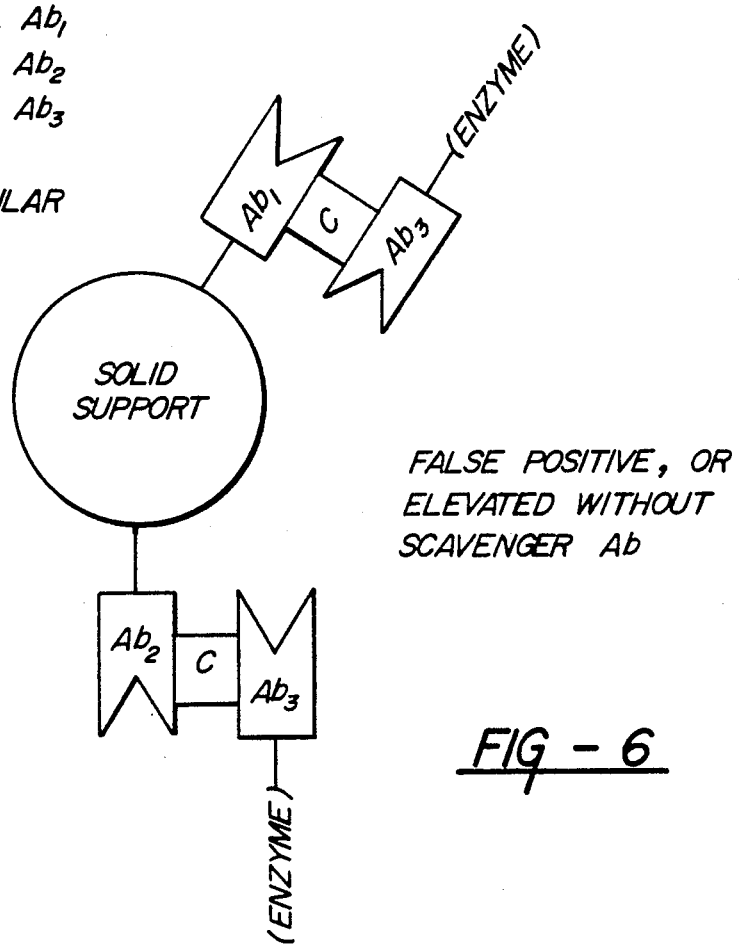
Figure 7:
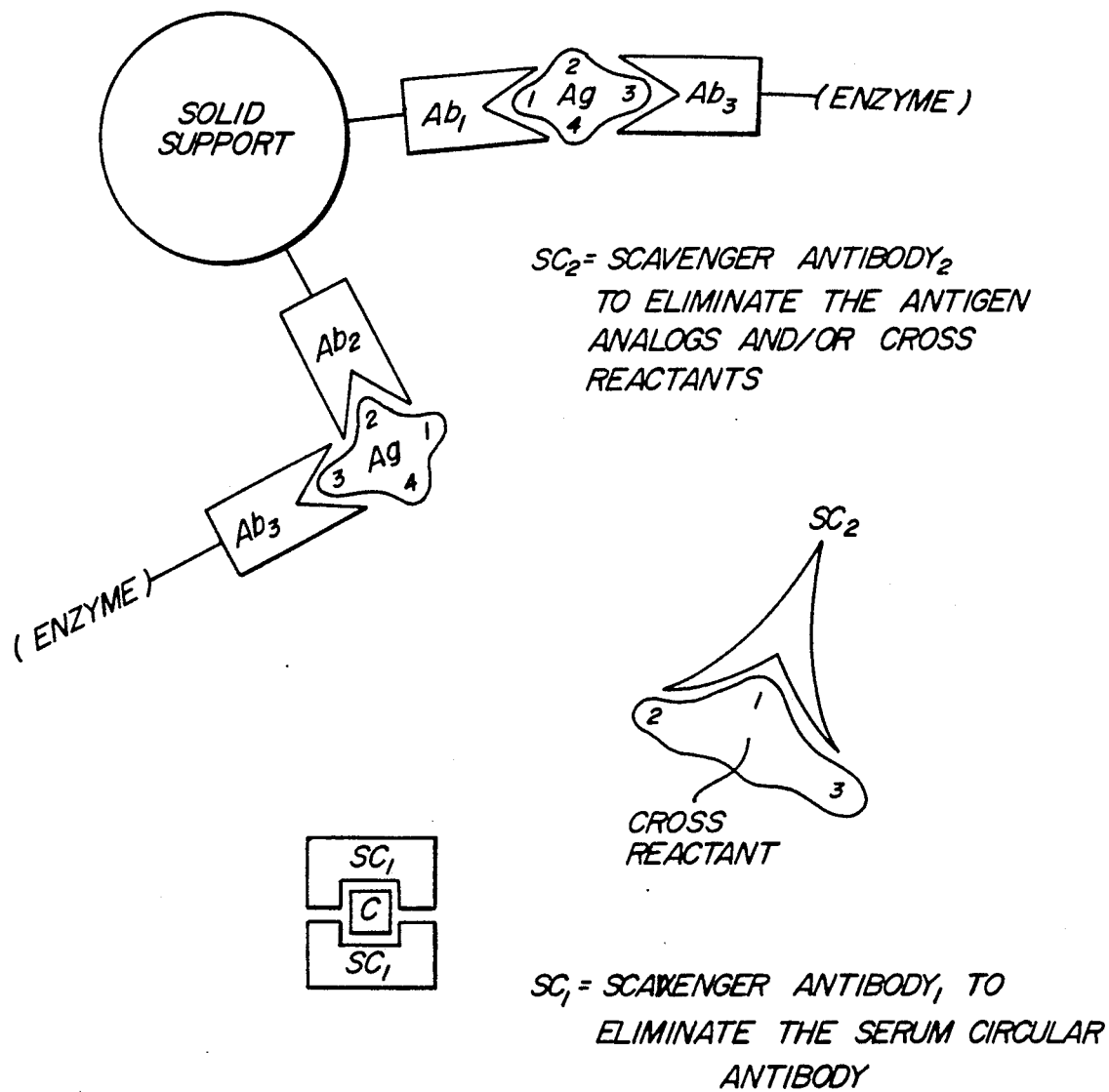

The method employs a unique reaction as follows:

(1) Dual monoclonal antibodies with divalent hCG reactivity and rapid kinetics characteristics are bonded by coating to a solid support. Such dual monoclonal antibodies are represented generally by $Ab_1$ $Ab_2$ as shown in FIGS. 5-7. The combination of divalent reactivity and rapid kinetics minimizes the incubation times necessary for high sensitivity.

(2) Another two monoclonal antibodies with C-terminal beta subunit reactivity and different affinity ($10^{12}$ liters/mole) are conjugated to a suitable enzyme or tagged with $I^{125}$ and are added to the antibody coated solid support.

(3) Endogenous hCG from the patient sample urine or serum is attached to the antibodies on the solid phase being thus bound to the solid support; the hCG also is reacted with the antibody-enzyme conjugate or antibody tagged with $I^{125}$ to complete the sandwich mechanism.

(4) Scavenger monoclonal antibody, as follows:

(a) unlabeled scavenger monoclonal antibody with beta subunit selectivity but low hCG affinity is present in the reaction to prevent any possible cross reactivity from analogs of homologous reactivity.

(b) unlabeled scavenger monoclonal antibody which is specific to human IgG, IgM, IgE, but no selectivity to hCG is present in the reaction to prevent any possible auto-immune antibody interference from pseudo (false) elevated or positive reactivity.

(c) unlabeled scavenger monoclonal antibody which is specific to any antigen except hCG, or normal mouse antibody is present in the reaction to prevent any possible interference in the reaction due to human antibody against mouse IgG, and (d) scavenger monoclonal antibody with beta subunit selectivity but low hCG affinity (less than $10^8$ liter/mole) is present in the reaction to prevent any high-dose hook effect.

HCG (EIA)

Label duplicate reaction tubes for all patients, standards and controls.

(1) Pipette 0.025 ml of patient, control and standards into the appropriately labeled antibody coated tube.

(2) Add 0.2 ml of Antibody Enzyme Conjugate to each tube and mix gently shaking the test tube rack.

(3) Incubate all tubes for 30 minutes at room temperature.

(4) During the last 10 minutes of incubation, prepare a sufficient amount of Substrate Chromogen for the assay.

(5) Decant the entire contents of all tubes and wash a minimum of five times by:

(a) filling the tube at least ¾ full with distilled water (b) decanting all liquid from the tube (c) blotting the rim of the tube onto absorbent paper to remove all water following the final rinse (6) Add 0.3 ml of Chromogen-Diluent mixture to all tubes and to one additional blank reaction tube. All tubes should be filled within two minutes or the addition should be timed in convenient intervals.

(7) Incubate all tubes for 10 minutes and avoid exposure to direct sunlight.

(8) Dispense 1.0 ml of 1N $H_2SO_4$ to all tubes and mix gently by vortexing within two minutes or at the same intervals as in step #6.

(9) Determine the absorbance of patients, controls and standards at 452 nm against the substrate blank tube within one hour of acid addition.

CALCULATION OF RESULTS—(Quantitative Assay)

If the analysis of the final color reaction is performed on a Spectra I spectrophotometer (Leeco Diagnostics, Inc.), the data reduction is automatic after selecting the hCG program module. Any spectrophotometer capable of accurately determining at 452 nm may be substituted. However, the instrument must accept 12 mm test tubes or it will be necessary to transfer the liquid to a suitable cuvette. The hCG value of patient and control samples is obtained as follows:

(1) Determine the optical density of each standard, control and patient sample at 452 nm against the reagent blank.

(2) Construct a standard curve by plotting the mean optical density of each standard (y-axis) against its concentration (x-axis) on rectilinear graph paper.

(3) Determine the value of patient and control samples by reference to the curve. Find the absorbance value on the y-axis and extend a horizontal line to the curve. At the point of intersection extend a vertical line to x-axis and read the corresponding hCG concentration for the unknown.

SAMPLE DATA

| Tube # | Sample | Average O.D. (452 nm) | hCG mIU/ml |
|---|---|---|---|
| 1, 2 | 0 mIU/ml | 0.055 | |
| 3, 4 | 5.0 mIU/ml | 0.130 | |
| 5, 6 | 10.0 mIU/ml | 0.210 | |
| 7, 8 | 25.0 mIU/ml | 0.430 | |
| 9, 10 | 50.0 mIU/ml | 0.730 | |
| 11, 12 | 100.0 mIU/ml | 1.180 | |
| 13, 14 | 200.0 mIU/ml | 1.750 | |
| 15, 16 | Control I | 0.235 | 12.5 |
| 17, 18 | Control II | 1.325 | 125.0 |
| 19, 20 | Patient #1 | 0.810 | 58.0 |
| Example: | Patient Serum | | |

Average net optical density of patient = 0.810
By interpolation, the O.D. of 0.810 is found to yield 58.0 mIU/ml of hCG

FLOW CHART (QUANTITATIVE)

| | Sample | Enzyme Conjugate | | Chromogen-Diluent | | 1 N H$_2$SO$_4$ | | |
|---|---|---|---|---|---|---|---|---|
| 0.0, 5, 10, 25, 50, 100, 200 mIU/ml Standard | 0.025 ml | 0.2 ml | Mix & incubate at room temp. for 30 min. | Decant & wash 5 times | 0.3 ml | Incubate at room temp. for 10 min. | 1 ml | Read all tubes at 452 nm |
| Positive Control | 0.025 ml | 0.2 ml | | | | | | |
| Negative Control | 0.025 ml | 0.2 ml | | | 0.3 ml | | 1 ml | |
| Patient | 0.025 ml | 0.2 ml | | | 0.3 ml | | 1 ml | |
| Substrate Blank | — | — | | | 0.3 ml | | — | |

SERUM OR URINE (QUALITATIVE)

(1) Add 0.1 ml (2 drops) of patient sample (serum or urine) and 0.1 ml (2 drops) of positive, negative or reference sample if desired into an appropriately labeled antibody coated reaction tube.

(2) Add 0.2 ml (4 drops) of Enzyme Conjugate into each tube.

(3) Mix gently by shaking the test tube rack and allow the tube to stand undisturbed for 5 minutes at room temperature.

(4) Decant the entire contents of the tube and "wash" a minimum of five times by:

(a) filling the tube at least ¾ full with distilled water (b) decanting all liquid from the tube (c) blotting the rim of the tube onto absorbent paper to remove all water following the final wash (5) Add five (5) drops of Substrate Diluent directly into the tube and add (1) one drop (0.05 ml) of Substrate Chromogen.

(6) Mix gently by shaking the test tube rack and allow to stand undisturbed at room temperature for 5 minutes.

(7) Compare the intensity of the blue color in the patient tube to that of the reference. A deeper blue color in the patient tube is a positive reaction. A colorless or blue color of equal intensity to the reference or of less intensity should be considered as a negative finding.

HCG (IRMA TAGGED WITH I$^{125}$)

Procedure Instructions—Quantitative

Label duplicate 12×75 mm test tubes for all patients, controls and standards.

(1) Pipet 0.05 ml of patient sample and each of the 0.0, 5.0, 10, 25, 50, 100 and 200 mIU/ml standards into the appropriately labeled tubes.

(2) Add one Antibody Coated Bead to all tubes.

(3) Add 0.1 ml of the I$^{125}$ Anti-hCG Tracer solution to all tubes and shake the test tube rack gently to assure complete mixing.

(4) Cover all tubes with parafilm and incubate at 39° C. for one (1) hour.

(5) Add 2.0 ml of distilled water to each tube and decant the entire contents of the tube.

(6) Repeat the wash procedure step #5 and allow the tubes to remain inverted for a few minutes and gently blot the rims of the tubes onto absorbent paper.

(7) Determine the radioactivity remaining in each tube by counting in a gamma scintillation counter for not less than the time required to achieve 10,000 counts in the 200 mIU/ml standard.

CALCULATIONS—Quantitative (1) Determine the mean count rate for each patient, control and reference standard if replicate samples were performed.

(2) Plot the concentration of each standard directly against its count rate on rectilinear graph paper.

(3) Obtain the value of patient hormone by reference to the standard curve.

SAMPLE DATA

| Tube | Sample | Average CPM | nCG Conc. |
|---|---|---|---|
| 1, 2 | 0.0 mIU/ml | 920 | |
| 3, 4 | 5.0 mIU/ml | 2120 | |
| 5, 6 | 10 mIU/ml | 3287 | |
| 7, 8 | 25 mIU/ml | 6260 | |
| 9, 10 | 50 mIU/ml | 10980 | |
| 11, 12 | 100 mIU/ml | 19603 | |
| 13, 14 | 200 mIU/ml | 27396 | |
| 15, 16 | Patient "A" | 4673 | 17.5 mIU/ml |
| 17, 18 | Patient "B" | 11619 | 54.0 mIU/ml |
| 19, 20 | Patient "C" | 21883 | 117.0 mIU/ml |

Example: Patient "A" shows an average count rate of 4673 cpm. By interpolation from the standard curve, it can be seen that this activity corresponds to an hCG level of 17.5 mIU/ml.

FLOW CHART

| Sample | Serum | | Tracer | | Water | |
|---|---|---|---|---|---|---|
| 0.0, 5.0, 10, 25, 50, 100 and 200 mIU/ml Standard | 0.05 ml | Add 1 bead to all tubes | 0.1 ml | Shake & incubate at 37° C. for | 2.0 ml | Wash twice and |

-continued

| FLOW CHART | | | | |
|---|---|---|---|---|
| Sample | Serum | Tracer | | Water |
| Positive Control | 0.05 ml | 0.1 ml | 60 min. | 2.0 ml count |
| Negative Control | 0.05 ml | 0.1 ml | | 2.0 ml |
| Patient | 0.05 ml | 0.1 ml | | 2.0 ml |

The effect of a scavenger antibody on the degree of cross reactivity on the BhCG assay Table 1 and Table 2.

TABLE 1

Effect of Scavenger Antibody on Cross Reactivity in BhCG EIA

| Standard (mIU/ml) | No Scavenger | | | Scavenger | | |
|---|---|---|---|---|---|---|
| | Absorbance | hCG (mIU/ml) | % Cross | Absorbance | hCG (mIU/ml) | % Cross |
| 0 | 0.013 | | | 0.012 | | |
| 6 | 0.066 | | | 0.041 | | |
| 25 | 0.222 | | | 0.126 | | |
| 50 | 0.456 | | | 0.236 | | |
| 200 | 1.738 | | | 0.91 | | |
| Specimen LH500 | 0.076 | 8 | 1.6 | 0.025 | 2 | 0.4 |

TABLE 2

Effect of Scavenger Antibody on Cross Reactivity in BhCG IRMA

| Standard (mIU/ml) | No Scavenger | | | Scavenger | | |
|---|---|---|---|---|---|---|
| | CPM | hCG (mIU/ml) | % Cross | CPM | hCG (mIU/ml) | % Cross |
| 0 | 294 | | | 300 | | |
| 5 | 2739 | | | 2185 | | |
| 10 | 5130 | | | 4159 | | |
| 20 | 9507 | | | 7215 | | |
| 40 | 17,399 | | | 13,500 | | |
| 80 | 33,015 | | | 26,180 | | |
| 160 | 62,593 | | | 46,052 | | |
| Specimen LH1000 | 24,377 | 48 | 4.8 | 2915 | 7 | 0.7 |

TABLE 3

Effect of Scavenger Antibodies on Patient HCG Samples Containing an Anti-mouse IgG

| Patient Number | Without Scavenger Ab | HCG TEST* With Scavenger Ab | Patient Diagnosis |
|---|---|---|---|
| 1 | 25 mIU | 25 mIU | Pregnancy |
| 2 | 500 mIU | 500 mIU | Pregnancy |
| 3 | >500 mIU (false positive) | Not Detectable | Autoimmune Disease (non-pregnant) |
| 4 | 200 mIU (false positive) | Not Detectable | RA (non-pregnant) |
| 5 | >500 mIU (false positive) | Not Detectable | RA (non-pregnant) |
| 6 | 300 mIU (false positive) | Not Detectable | Autoimmune Disease (non-pregnant) |
| 7 | >500 mIU (false positive) | Not Detectable | RA (non-pregnant) |
| 8 | >500 mIU (false positive) | Not Detectable | RA (non-pregnant) |
| 9 | 100 mIU (false positive) | Not Detectable | RA (non-pregnant) |
| 10 | 40 mIU (false positive) | Not Detectable | RA (non-pregnant) |

*By Using Double monoclonal Ab Sandwich Assay Data EIA
RA = Rheumatoid Arthritis Scavenger antibody in hCG assays is used to virtually eliminate LH cross reactivity. The scavenger antibody is characterized by beta subunit selectivity with a low affinity for hCG but high affinity for cross reactants such as LH, FSH, and TSH that share a common alpha subunit. The effect of a scavenger antibody on the degree of cross reactivity on a BhCG IRMA assay is shown in Table 1.

LH(500) is a serum pool containing 500 mIU/ml luteinizing hormone. The LH pool when run as an unknown for BhCG in the absence of scavenger antibody showed 8 mIU/ml interference. In the presence of scavenger antibody, the cross reactivity was reduced to 2 mIU/ml. In other words, the percent cross reactivity of LH is reduced from 1.6% to 0.4% by incorporating scavenger antibody in the assay (Table 1). In Table 2, the LH 1000 mIU/ml pool, when run as an unknown for BhCG using the IRMA BhCG assay, gave a value of 48 mIU/ml and had a cross reactivity of 4.8%. The same pool in the presence of scavenger antibody gave a BhCG value of 7 mIU/ml and the cross reactivity was reduced to 0.7% (Table 2).

Figure 8:
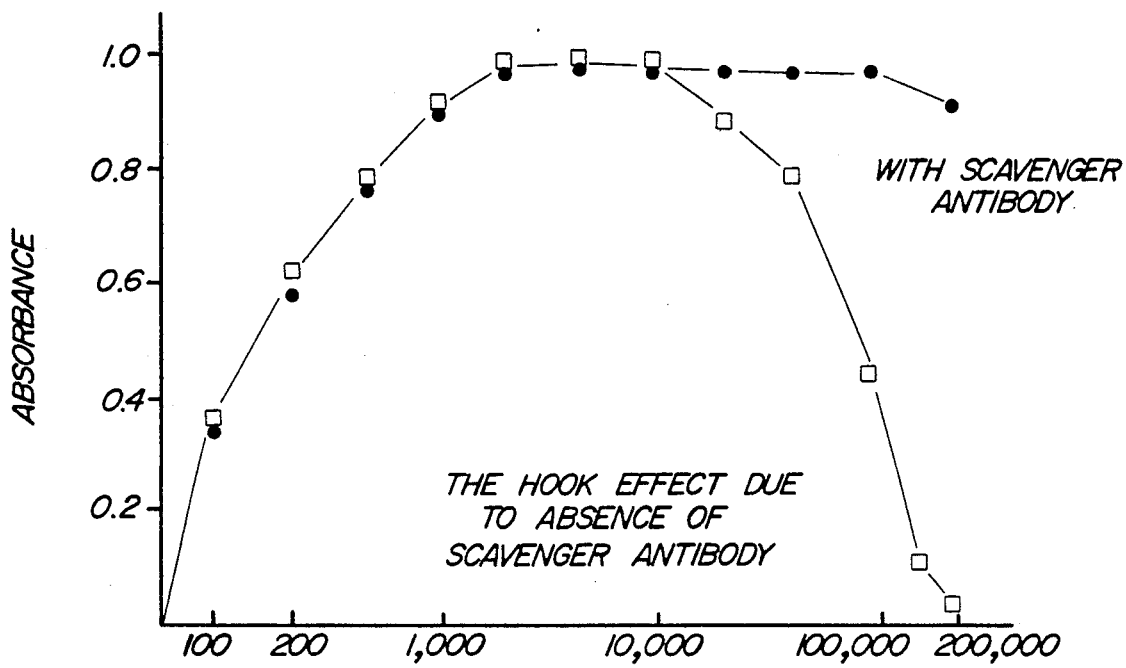
FIG. 8 is a plot of absorbance vs. BhCG concentration in an assay according to the invention showing the effect of scavenger antibody on the hook effect at high analyte concentration.

The second scavenger antibody in the assay has as its purpose to reduce the high-dose hook effect to which many two-site immunometric assays are subject. In a sandwich assay, the antibody (number of binding sites)

available to the antigen is limited by the surface area of the solid support, and the amount of antibody in the conjugate. The binding of protein to antibodies is saturable and reaches a plateau at high antigen concentrations. If excess antigen is present for the amount of antibody, the reaction will be inhibited (a sandwich is not formed); this is known as the prozone phenomenon or hook effect, for example, at a point where a specimen having a high concentration of antigen (e.g., 100,000 mIU/ml) when no scavenger antibody is present in the reaction, will have the same or lower absorbance as a 100 mIU/ml specimen (FIG. 8).

Figure 9:
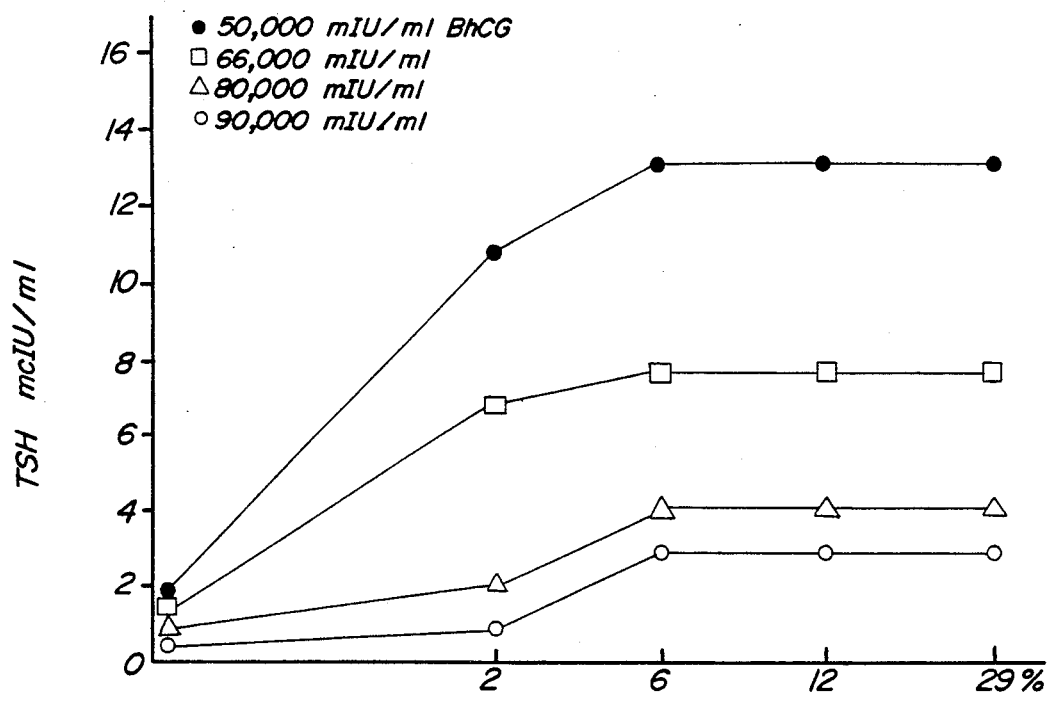
FIG. 9 is a plot (TSH concentration vs. % scavenger antibody) of a family of curves representing fluid specimens having various concentrations of the endogenous cross-reactant hCG, with and without scavenger antibody.

Concentrations of BhCG in pregnancy often exceed 100,000 mIU/ml; therefore it is essential that the standard curve of a BhCG assay give reliable results at high concentrations. Immunometric assays with scavenger antibody according to the invention typically do not exhibit a hook effect at high concentration, e.g. at 150,000 mIU/ml or more. The scavenger has a high affinity for LH and a low affinity for BhCG. It binds the BhCG only at high concentrations when excess antigen is present, thus extending the standard curve. FIG. 9 illustrates the prozone with, and without, scavenger antibody present in the reaction.

The third and fourth scavenger antibody have as their purpose to eliminate false positives due to anti-mouse antibodies or autoimmune antibody in the specimens. These antibodies are capable of cross linking the labeled antibody with the solid phase antibody in the two-site assay, thus giving erroneous high values for the analyte. Two-site immunometric assays are particularly prone to interference by antibodies against the specific immunoglobulin being used in the assay. The anti-mouse immunoglobulins appear to be "rheumatoid-like" factors possibly found in auto-immune diseases. The presence of scavenger antibody in the reaction prevents cross-linking with human anti-mouse IgG and avoids pseudo increased results. In the visual pregnancy test, some negative serum for BhCG gave positive results when no scavenger antibody was present as shown in Table 3. Upon employment of scavenger antibody in the reaction the sera yield negative results (Table 3).

These results show that the presence of scavenger antibody in immunometric assays improves the specificity and sensitivity by reducing interference and cross reactivity by analogs, reducing the hook effect and eliminating false positive values caused by circulating antibodies to mouse IgG.

The same procedure of Example 1 can be used for the immunoassay of other hormone substances such as HTSH, LH, HFSH, human prolactin, insulin, AFP, CEA, ferritin, and thymosin peptide.

EXAMPLE II

TSH (Thyroid Stimulating Hormone immunometric assay) (Simultaneous Assay)

The method employs a unique reaction as follows:

(1) Dual monoclonal antibodies with divalent TSH reactivity and very rapid kinetics characteristics are bonded to a solid support.

(2) Other different, dual monoclonal antibodies with beta subunit TSH selectivity and high affinity, paired with the antibody on the solid support, are conjugated to an enzyme or tagged with tracer $I^{125}$ and added to the reaction, (3) Scavenger monoclonal antibody, as follows:

(a) unlabeled scavenger monoclonal antibody with beta hCG subunit selectivity but no TSH affinity is present in the reaction to prevent any possible cross reactivity of LH or interference of hCG (b) unlabeled scavenger monoclonal antibody which is specific to human IgG, IgM and IgE but no selectivity to TSH is present in the reaction to prevent any possible auto-immune antibody interference which would produce falsely elevated reactivity, and (c) unlabeled scavenger monoclonal antibody which is specific to any antigen except TSH, or normal mouse antibody, is present in the reaction to prevent reaction with any possible human antibody against mouse IgG.

TSH EIA (Enzymeimmunoassay in Vitro Diagnostic Test Kit for the Detection of Thyroid Stimulating Hormone in Serum)

Label 12×75 mm test tubes for each specimen, standard and control.

(1) Pipette 0.1 ml of patient sample, control and each of 0.0, 1.0, 5.0, 20 and 50 mcIU/ml standards into the appropriate tube.

(2) Add 0.1 ml of Enzyme Conjugate to each tube and mix gently by shaking the test tube rack.

(3) Using a plastic forcep, add one antibody coated bead to each tube and mix gently again.

(4) Incubate all tubes at 37° C. for 15 minutes.

(5) During the incubation period, prepare the OPD substrate solution.

(6) After incubation, wash each tube at least four times with a minimum of 3 ml of distilled water per wash.

(7) Washing is most effective when the bead is dislodged from the tube wall during water additions. To decant liquid from the tubes, place in a decanting rack or firmly cover with a decanting screen and invert the rack over the sink. After the final wash, place the rack of inverted tubes onto absorbent paper and blot the excess liquid before placing upright.

(8) Pipette 0.3 ml of substrate solution to each tube and into an additional blank tube.

(9) Incubate all tubes in the dark at room temperature for ten minutes.

(10) Dispense 1.0 ml of 1N $H_2SO_4$ to all tubes and mix thoroughly by vortexing.

(11) Determine the absorbance of all tubes at 492 nm against the reagent blank.

| FLOW CHART (Tube Method) | | | | | |
|---|---|---|---|---|---|
| Sample | Serum | Enzyme Conjugate | OPD | | $H_2SO_4$ |
| 0, 1, 5, 20 and 50 mcIU/ml | 0.1 ml | 0.1 ml | mix gently, add 1 bead to all tubes, mix again & incubate at 37° C. for 15 | 0.3 ml | incubate at R.T. for 10 min. in the dark | 1.0 ml |
| Level I | 0.1 ml | 0.1 ml | | 0.3 ml | | 1.0 ml |
| Level II | 0.1 ml | 0.1 ml | | 0.3 ml | | 1.0 ml |
| Patient | 0.1 ml | 0.1 ml | | 0.3 ml | | 1.0 ml |

-continued

FLOW CHART (Tube Method)

| Sample | Serum | Enzyme Conjugate | OPD | H$_2$SO$_4$ |
|--------|-------|------------------|-----|-------------|
|        |       | mins. & wash at least 4 times | | |

Read all tubes at 492 nm against the reagent blank.

TSH, hCG, LH, and FSH have common alpha subunits. The antibodies reacted with the alpha subunit of TSH produce non-specific binding and cross reactions with these hormones. Traditional sandwich assays utilize only one monoclonal antibody pair. In most cases, the monoclonal antibody binds all analogs that also contain alpha subunits. Usually, this is not a problem unless the sample contains high levels of analogs, as in pregnancy where hCG levels become extremely high. When the analog (hCG) exists in high concentrations, the hCG alpha subunits will also be bound to the solid phase antibody. If the hCG level is high enough, it will fill all the binding sites, and block or interfere with TSH binding, especially the binding of small quantities of TSH, preventing the formation of the TSH Ab-Ag-Ab sandwich. As a result, all the TSH present in the sample is not measured and the value for TSH will be falsely depressed. TSH two-site immunometric assays according to the present invention incorporate a scavenger monoclonal antibody that has high affinity for hCG and no TSH binding; it binds excess hCG and prevents interference. Interference of hCG in a monoclonal TSH assay was measured by adding increasing concentrations of hCG to a known concentration of TSH. In the presence of scavenger antibody all the TSH is measured, while when no scavenger antibody is present, there is a marked decrease in the TSH value as shown in Table 4. The titration curve of scavenger antibody for the TSH assay, in the presence of increased concentrations of BhCG, is illustrated in FIG. 5.

TABLE 4

Effect of Scavenger Antibody on Interference in TSH IRMA

| Specimen hCG Value | Theoretic* TSH Value (mcIU) | TSH Value (mcIU) Without Scavenger Ab | TSH Value (mcIU) With Scavenger Ab |
|--------|--------|--------|--------|
| 50,000 mIU | 14.2 | 1.3 | 13.9 |
| 66,000 mIU | 7.5 | 0.9 | 7.6 |
| 80,000 mIU | 4.8 | 0.8 | 4.7 |
| 90,000 mIU | 2.7 | 0.0 | 2.8 |

*Results obtained by using double antibody competitive assay.

The second scavenger antibody is to eliminate falsely elevated TSH values due to anti-mouse antibodies or autoimmune antibody in the specimens. These antibodies are capable of cross linking the labeled antibody with solid phase antibody in the two site assay, thus giving erroneous high values for the analyte.

Two-site immunometric assays are particularly prone to interference by antibodies against the specific immunoglobulin being used in the assay. The anti-mouse immunoglobulins appear to be "rheumatoid-like" factors possibly found in auto-immune diseases. The presence of scavenger antibody in the reaction prevents cross-linking with human anti-mouse IgG and avoids pseudo increased results.

Upon employment of scavenger antibody in the reaction the sera yields results (Table 5).

TABLE 5

Effect of Scavenger Antibodies on Patient TSH samples.

| Patient # | Theoretic TSH Value (uIU) | TSH Value (uIU) Without Scavenger Ab | TSH Value (uIU) With Scavenger Ab | Patient Diagnosis |
|---|---|---|---|---|
| 1 | 2.5 | 2.5 | 2.43 | Euthyroid |
| 2 | 0.2 | 0.25 | 0.18 | Hyperthyroid |
| 3 | 15.0 | 16.0 | 15.3 | Hypothyroid |
| 4 | 2.2 | 52.0 | 2.4 | Autoimmune-Disease |
| 5 | 2.5 | 18.0 | 2.2 | RA |
| 6 | 2.3 | 10.0 | 2.9 | RA |
| 7 | 1.8 | 13.0 | 2.2 | RA |

RA = Rheumatoid Arthritis

HCG (Membrane Assay Method)

The method optionally is carried out in assay device of the type shown in the drawings and employs a reaction as follows:

(1) Polyclonal antibodies with divalent hCG reactivity and very rapid kinetics characteristics are bonded to the solid phase (nylon membrane, latex particle membrane, polystyrene membrane, and the like).

(2) Other monoclonal antibodies with C-terminal beta subunit reactivity are conjugated to a suitable enzyme (e.g., alkaline phosphatase). Three scavenger monoclonal antibodies are also contained in this mixture.

(a) Unlabeled scavenger monoclonal antibody with beta subunit selectivity but low hCG affinity is present in the reaction.

(b) Unlabeled scavenger monoclonal antibody which is specific to human IgG, IgM, and IgE, but no selectivity to hCG is present in the reaction.

(c) Unlabeled scavenger monoclonal antibody which is specific to any antigen except hCG and normal mouse antibody, is present in the reaction.

(3) Endogenous hCG from patient sample urine or serum is added to the membrane surface and is thus bound to the solid support. The patient sample is added to the reaction preferably through a filter assembly onto a membrane surface employing an assay device such as shown in the drawings. Endogenous hCG that reacts with the antibody-enzyme conjugate completes the sandwich formation.

(4) Substrate is added to the membrane surface. The appearance of a positive (+) sign indicates hCG at a concentration greater than 25 mIU/ml. The appearance of a negative (−) sign indicates hCG at a concentration less than 25 mIU/ml.

URINE (Qualitative)

(1) Remove the reaction container or cube from its protective package; do not remove the pre-filter from the container top.

(2) Using a transfer pipette, add 5 drops (0.5 ml) of sample onto the pre-filter cap of any appropriately labeled reaction cube. Allow the sample to soak through the pre-filter (approx. 10 seconds).

(3) Add 3 drops (0.2 ml) of Enzyme conjugate to the center of the pre-filter. Allow the solution to soak through the pre-filter and incubate for one minute.

(4) At the end of the incubation, remove and discard the pre-filter. Add 10 drops (1.0 ml) of Substrate Reagent onto the reaction membrane. Allow the color to develop for 3 minutes.

(5) Positive (+) results can be observed in less than 20 seconds but the full development time is required to confirm negative results. The resulting symbol should be read after 3 minutes of color development. The symbol is stable for up to one hour, however, the background color will increase during this time.

SERUM (Qualitative)

(1) Label one specimen cup for each patient, reference and control.

(2) Using a transfer pipette, add 3 drops (0.2 ml) of serum sample into the appropriately labeled specimen cup.

(3) Add 3 drops (0.2 ml) of Enzyme Conjugate into each specimen cup. Mix gently by shaking the cup and allow to stand at room temperature for 2 minutes.

(4) Remove the reaction cube from its protective package. Do not remove the pre-filter from the cube top.

Figure 3:
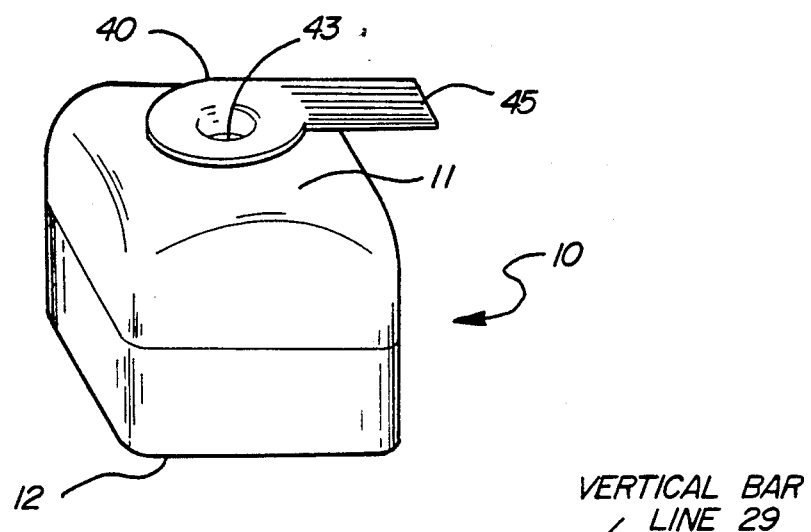
FIG. 3 is a view in perspective of the container device of FIG. 1 sealed with the closure of FIG. 2.
Figure 4A:
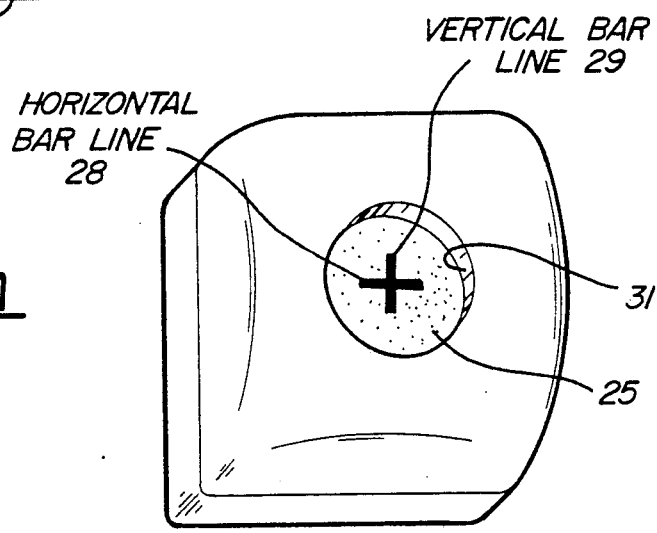
FIGS. 4A, 4B, and 4C are top views of the container device with the closure removed showing respectively the result obtained after testing three different samples: the appearance of intersecting vertical and horizontal bars signifying a positive sample; a negative sample; and the absence of a color reaction signifying an improper test or deterioration of reagents.
Figure 4B:
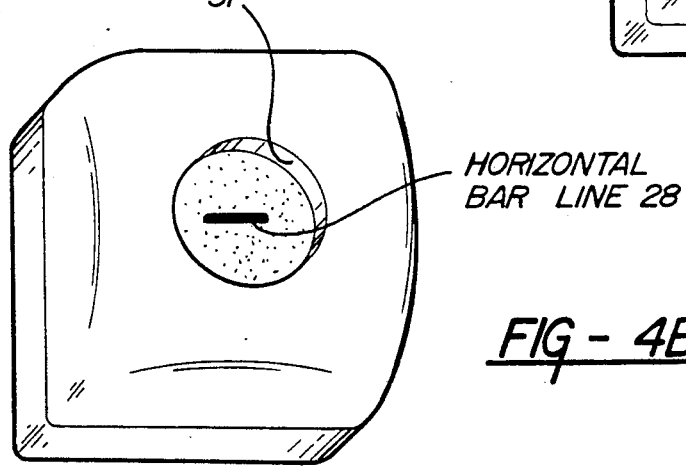
Figure 4C:
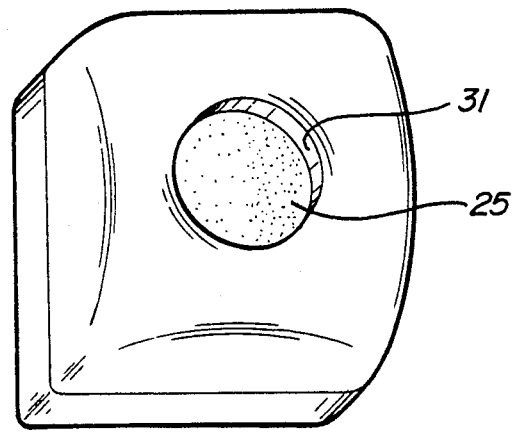

(5) At the end of the incubation, pour the entire contents of the specimen cup to the center of the pre-filter (FIG. 3). Allow the sample to soak through the pre-filter.

(6) Remove and discard the filter.

(7) Add 10 drops (1.0 ml) of Substrate Reagent onto the reaction membrane (FIGS. 4a, 4b, 4c). Allow the color to develop for 3 minutes.

(8) Positive (+) results can be observed in less than 20 seconds but the full development time is required to confirm negative results. The resulting symbol should be read after 3 minutes of color development. The symbol is stable for up to one hour, however, the background color will increase during this time.

INTERPRETATION OF RESULTS

1. A plus (+) indicates a specimen with elevated levels of hCG. Light color development on the vertical line should be interpreted as a positive result even if its intensity is less than the horizontal bar. The vertical bar indicates hCG concentrations greater than 25 mIU/ml.

2. A minus (−) indicates the absence of detectable hCG.

3. Reaction cubes that do not result in either a plus (+) or a minus (−) indicate the improper additional of reagents or deterioration of reagents.

The effect of a scavenger antibody on the degree of cross reactivity on a BhCG-Membrane-EIA assay is shown in Table 6.

TABLE 6

Effect of scavenger antibody on cross reactivity in membrane-EIA βhCG assay.

| Patient # | No Scavenger Antibody | | With Scavenger Antibody | Clinical Diagnosis |
|---|---|---|---|---|
| | Obtained Value | Actual Value | Obtained Value | |
| 1 | − | − | − | Normal male |
| 2 | + | + | + | Normal pregnancy |
| 3 (LH500) | + | − | − | Non-pregnancy |
| 4 (RA) | + | − | − | Non-pregnancy |
| 5 (RA) | + | − | − | Non-pregnancy |
| 6 (RA) | + | − | − | Non-pregnancy |

RA = Rheumatoid Arthritis

EXAMPLE III

Hepatitis B Surface Antigen Test

The $HB_s$ EIA method is a solid phase enzyme immunoassay system which utilizes a sandwich technique to measure $HB_s$ antigen levels in serum plasma or recalcified plasma. The method employs a unique multiple antibody reaction as follows:

(1) Dual monoclonal antibodies with $HB_s$ (adw, ayw) selectivity and very rapid kinetics characteristics are bonded to a plastic support. The use of two such antibodies minimizes the incubation times necessary for high sensitivity and high specificity.

(2) Polyclonal antibodies with $HB_s$ (adw, ayw) selectivity and high affinity are conjugated to an enzyme and added to the reaction.

(3) The "scavenger monoclonal antibody" with no $HB_s$ selectivity is present in the reaction to prevent any possible auto-immune antibody and human antibody against mouse IgG interference from falsely elevated or positive reactivity.

$HB_s$ Ag Test Procedure:

(1) Label 12×75 mm antibody coated test tubes for each specimen, standard and control (negative and positive).

(2) Pipette 0.1 ml of patient sample, positive control, negative control and reference standards into the appropriately labeled tube.

(3) Add 0.2 ml of enzyme conjugate to all wells and mix gently.

(4) Incubate all tubes at room temperature (15°–25° C.) for 30 minutes.

(5) Ten to fifteen minutes before the end of the incubation, prepare the substrate solution according to the following procedure;
5 parts of chromogen diluent
1 part of chromogen (6) After incubation, wash each tube at least four times with a minimum of 3.0 ml of distilled or tap water per tube each wash.

(7) Pipette 0.3 ml of substrate solution to each tube and into an additional blank tube.

(8) Incubate all tubes at room temperature for ten minutes.

(9) Record results or add 1.0 ml of 1N $H_2SO_4$ to all tubes and mix thoroughly by vortexing.

(10) Determine the absorbance of all tubes at 450 nm against the reagent blank.

Interpretation of results

Positive = Any specimen which yields a blue color deeper than the reference tube Negative = Any specimen which yields a colorless or faintly blue reaction (less blue than reference standard tube)

The effect of a savenger antibody on the degree of interference on a $HB_s$-enzymeimmunassay is shown in Table 7.

TABLE 7

Effect of scavenger antibody on cross reactivity in EIA-$HB_s$ assay.

| | No Scavenger Antibody | | With Scavenger Antibody | |
|---|---|---|---|---|
| Patient # | Obtained Value | Actual Value | Obtained Value | Clinical Diagnosis |
| 1 | − | − | − | Normal patient |
| 2 | + | + | + | Hepatitis infected Patient |
| 3 (RA) | + | − | − | No Heptatitis Infection |
| 4 (RA) | + | − | − | No Hepatitis Infection |
| 5 (RA) | + | − | − | No Hepatitis Infection |

RA = Rheumatoid Arthritis

BIBLIOGRAPHY

Hunter W M, Budd P S. Circulating antibodies to ovine and bovine immunoglobulin in healthy subjects: a hazard for immunoassays [Letter] Ibid 1980; ii:1136.

Howanitz P J, Howanitz J H, Lamberson H V, Ennis K M incidence and mechanism of spurious increases in serum thyrotropin Clin. Chem. 1982; 28: 427-31.

Lazarus J H, John R, Ginsburg J, et. al. Transient neonatal hyperthyrotropinaemia: a serum abnormality due to transplacentally acquired antibody to thyroid stimulating hormone. Br. Med. J. 1983; 286: 592-4.

Addison G M, New developments in immuoradiometric assay. In: Hayes E. Goswitz A, Murphy F, eds. Radioimmunoassay and related procedures in medicine. Vienna: Int. At. Energy Agency, 1974; 131-47.

Price A M, Brothman B, Jaas D, Inksam H. Specificity of the direct solid phase immunoasssay for the detection of hepatitis B antigen. Lancent 1973; i: 1346-50.

Hunter W M, Budd P S. Circulating antibodies to ovine and bovine immunoglobulins in healthy subjects: a hazard for immunoassay. Lancet 1980; ii: 1136.

Howanitz P J, Hawanitz J H, Lamberson H V, Ennis K M. Incidence and mechanism of spurious increases in serum thyrotropin. Clin. Chem. 1982; 28: 427-31.

Hunter W M, Bennie J G, Budd P S, et. al. Immunoradiometric assays using monoclonal antibodies. In: Hunter W M, Corrie J E T, eds., Immunoassays for clinical chemistry. Edinburgh: Churchhill Livingstone, 1983: 531-44.

Cusick C F, Mistry K, Addison G M. Interference in two-site immunometric assay for thyotropin in a child [Letter]. Clin. Chem. 1985; 31: 348-9.

Bock J L, Fugiuele J, Segen J C. Choriogonadotropin measured with the Tandem-E immunoenzymematic assay system. Clin. Chem. 1985; 31: 441-4.

Clark P M, Raggatt P R, Price C P. Antibodies interfering with immunometric assays [Letter] Clin. Chem. 1985; 31: 1762.

References
U.S. Patent Documents

| | | | |
|---|---|---|---|
| 3,935,074 | 1/1976 | Rubenstein et al. | 195/103.5R |
| 4,376,110 | 3/1983 | David et al. | 436/513 |
| 4,248,965 | 2/1981 | Mochida et al. | 435/7 |
| 4,514,505 | 4/1985 | Canfield et al. | 436/500 |
| 4,514,507 | 4/1985 | Secher et al. | 436/518 |
| 4,510,239 | 4/1985 | Miller et al. | 435/7 |
| 4,467,031 | 8/1985 | Gallati et al. | 435/7 |
| 4,595,661 | 6/1986 | Cragle et al. | 436/534 |
| 4,565,687 | 1/1986 | Khazaeli et al. | 424/1.1 |
| 4,632,901 | 12/1986 | Valkirs et al. | 435/5 |

What is desired to claim as our exclusive property in the invention, as described, is the following:

1. A storage-stable reagent kit for immunoassay of the antigen human chorionic gonadotropin (hCG) in an aliquot of body fluid, comprising:

(a) as a first component, a label conjugated to an antibody which is immunospecific for the hCG antigen;

(b) as a second component, an antibody immobilized by solid support means, the immobilized antibody being immunospecific for the hCG antigen;

(c) a further component that is a scavenger antibody characterized by both low affinity for the hCG antigen and high affinity for the cross reactant analogs luteinizing hormone (LH), follicle stimulating hormone (FSH), and thyroid stimulating hormone (TSH), the scavenger antibody being present in an amount sufficient to prevent unwanted reactivity between the antibody of said first component and the antibody of said second component with said antigen cross reactant analog of the hCG antigen;

(d) detection means responsive to the label for determining the presence thereof;

the components being constituted such that, when subjected to liquid phase incubation with an aliquot containing the hCG antigen, the cross reactant analogs are scavenged and the first and second components become mutually bound at immunospecific binding sites with the hCG antigen in sandwich relation thereby preventing said cross reactivity and enabling separation of the bound hCG antigen in solid form free of non-specific antigen and unbound labeled antibody.

2. A kit as in claim 1, wherein at least one of said first component and said second components includes a monoclonal antibody.

3. A kit as in claim 1, wherein said scavenger antibody is a monoclonal antibody.

4. A kit as in claim 1, wherein said scavenger antibody is a polyclonal antibody.

5. A kit as in claim 1, wherein said scavenger antibody is further characterized by selectivity for the beta subunit of hCG.

6. A kit as in claim 1, wherein said second component comprises an antibody immunospecific for the hCG antigen and immobilized upon a generally planar support in an area defining a vertical line extending at least part way thereacross;

wherein said support further includes a reagent adapted to react so as to bind the tracer conjugated antibody of the first component thereto and substantially not reactive with hCG, said reagent bound to said support in an area defining a horizontal line intersecting the vertical line, whereby the immunoassay of a fluid containing hCG causes reaction of both of said lines so as to form a plus sign and immunoassay of a fluid containing substantially no hCG causes reaction only of said horizontal line so as to form a minus sign.

7. A sensitive, rapid, and accurate immunometric assay for the antigen hCG in a sample of body fluid, hCG having two distinct amino acid chain subunits designated as alpha and beta, which assay comprises:

(a) contacting the sample with a labeled antibody specific to the antigen to form a soluble labeled complex of the antibody and antigen;

(b) contacting the sample with at least one unlabeled soluble scavenger antibody characterized by low affinity for hCG and high affinity for cross reactive substances LH, FSH and TSH so as to prevent the formation of a complex between the labeled antibody and the cross reactive substances which are present in said sample;

(c) contacting the soluble complex with another antibody which is specific to the hCG antigen, said other antibody being bound to a solid carrier; and (d) detecting the labeled antibody.

8. An assay as in claim 7, wherein the step of contacting the sample with a scavenger antibody comprises contacting the sample with a monoclonal antibody.

9. An assay as in claim 7, wherein the step of contacting the sample with a scavenger antibody comprises contacting the sample with an antibody having selectivity for the beta subunit of hCG.

10. An assay as in claim 7, wherein the step of contacting the sample with a scavenger antibody comprises contacting the sample with a polyclonal antibody.

* * * * *